US011172809B2

(12) United States Patent
Paris et al.

(10) Patent No.: US 11,172,809 B2
(45) Date of Patent: Nov. 16, 2021

(54) VISION PROBE WITH ACCESS PORT

(71) Applicant: Intuitive Surgical Operations, Inc., Sunnyvale, CA (US)

(72) Inventors: Michael D. Paris, San Francisco, CA (US); Lucas Gordon, Saratoga, CA (US); Tao Zhao, Sunnyvale, CA (US); Carol Reiley, San Francisco, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 393 days.

(21) Appl. No.: 14/181,024

(22) Filed: Feb. 14, 2014

(65) Prior Publication Data

US 2014/0235943 A1 Aug. 21, 2014

Related U.S. Application Data (60) Provisional application No. 61/765,496, filed on Feb. 15, 2013.

(51) Int. Cl.
*A61B 1/015* (2006.01)
*A61B 1/018* (2006.01)
(Continued)

(52) U.S. Cl.
CPC .......... *A61B 1/015* (2013.01); *A61B 1/00135* (2013.01); *A61B 1/00154* (2013.01);
(Continued)

(58) Field of Classification Search
CPC ..... A61B 1/273; A61B 1/2733; A61B 1/2736; A61B 1/31; A61B 1/00071; A61B 1/0008;
(Continued)

(56) References Cited

U.S. PATENT DOCUMENTS 5,343,853 A * 9/1994 Komi ................. A61B 1/00098
600/107
5,766,151 A * 6/1998 Valley ............... A61M 39/0247
604/103.07
(Continued)

FOREIGN PATENT DOCUMENTS

JP WO 2012132778 A1 * 10/2012 ......... A61B 1/00147

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Ryan N Henderson
(74) *Attorney, Agent, or Firm* — Haynes and Boone, LLP (57) ABSTRACT

An anatomical probe system comprises an elongated flexible body and an elongated probe extending within the flexible body. The probe has a distal opening at a distal face of a distal end and includes an outer wall defining a channel, an access port in the outer wall in communication with the channel, a one-way flow controller, and an image capture instrument secured to the outer wall at a location proximal of the distal opening. The access port is spaced proximally of the distal face of the distal end. The one-way flow controller includes a cover configured to move between an open position where the access port is uncovered and the channel is in fluid communication with an area adjacent to the elongated probe via the access port, and a closed position where the access port is covered and a migration of fluids through the distal opening is permitted.

19 Claims, 7 Drawing Sheets

(51) Int. Cl.
    *A61B 1/00* (2006.01)
    *A61B 1/12* (2006.01)
    *A61B 1/05* (2006.01)
(52) U.S. Cl.
    CPC ............ *A61B 1/018* (2013.01); *A61B 1/05* (2013.01); *A61B 1/126* (2013.01)
(58) Field of Classification Search
    CPC ............ A61B 1/00089; A61B 1/00091; A61B 1/00094; A61B 1/00098; A61B 1/00101; A61B 1/00135; A61B 1/00137; A61B 1/00142; A61B 1/00154; A61B 1/012; A61B 1/0125; A61B 1/015; A61B 1/018; A61M 2025/0183
    USPC ........ 600/104, 106, 107, 114, 121–125, 127, 600/129, 156–159, 170–173
    See application file for complete search history.

(56) References Cited

U.S. PATENT DOCUMENTS

| | | | | |
|---|---|---|---|---|
| 5,779,624 A | * | 7/1998 | Chang | A61B 1/00142 600/114 |
| 6,358,199 B1 | * | 3/2002 | Pauker | A61M 25/0113 600/102 |
| 6,475,187 B1 | * | 11/2002 | Gerberding | A61M 25/0054 600/435 |
| 6,702,781 B1 | * | 3/2004 | Reifart | A61M 25/104 604/96.01 |
| 2003/0153934 A1 | * | 8/2003 | Gerberding | A61M 25/0169 606/157 |
| 2004/0176742 A1 | * | 9/2004 | Morris | A61M 25/0075 604/537 |
| 2005/0038317 A1 | * | 2/2005 | Ratnakar | A61B 1/00105 600/101 |
| 2005/0065498 A1 | * | 3/2005 | Ferran | A61M 25/0075 604/528 |
| 2006/0252994 A1 | * | 11/2006 | Ratnakar | A61B 1/00179 600/173 |
| 2008/0171979 A1 | * | 7/2008 | Brown | A61F 2/958 604/103.04 |
| 2008/0249356 A1 | * | 10/2008 | Motai | A61B 1/00154 600/114 |
| 2008/0269559 A1 | * | 10/2008 | Miyamoto | A61B 1/31 600/116 |
| 2009/0043166 A1 | * | 2/2009 | Ishii | A61B 1/0011 600/130 |
| 2009/0182200 A1 | * | 7/2009 | Golden | A61M 25/09 600/153 |
| 2013/0331730 A1 | | 12/2013 | Fenech et al. | |
| 2014/0024897 A1 | * | 1/2014 | Inoue | A61B 1/00147 600/115 |

\* cited by examiner

VISION PROBE WITH ACCESS PORT

CROSS-REFERENCE TO RELATED APPLICATIONS

This application claims the benefit of U.S. Provisional Application 61/765,496 filed Feb. 15, 2013, which is incorporated by reference herein in its entirety.

FIELD

The present disclosure is directed to systems and methods for minimally invasive surgery, and more particularly to systems and methods for accessing a channel of a vision probe.

BACKGROUND

Minimally invasive medical techniques are intended to reduce the amount of tissue that is damaged during diagnostic or surgical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert surgical instruments to reach a target tissue location. To reach the target tissue location, the minimally invasive surgical instruments may navigate natural or surgically created connected passageways in anatomical systems, such as the lungs, the colon, the intestines, the kidneys, the heart, the brain, the circulatory system, or the like. To allow a clinician to visualize the passageways, often an endoscopic probe is fed through the passageways to capture and return images. As the endoscopic probe is advanced, body matter, such as blood, tissue, or mucus, accumulates on the end of the probe and obstructs the view of the passageways. Blockages of the passageways may also become an impediment to the clinician using the endoscopic probe. Improved systems and methods are needed to disrupt passageway blockages and clean the endoscopic probes in vivo.

SUMMARY

The embodiments of the invention are summarized by the claims that follow the description.

In one embodiment, an anatomical probe system comprises an elongated flexible body and an elongated probe extending within the flexible body. The probe has a distal end and includes an outer wall defining a channel. The probe also includes an access port in the outer wall in communication with the channel. The access port is spaced proximally of the distal end.

In another embodiment, a method of operating an anatomical probe system comprises providing an elongated flexible body including a passageway and providing an elongated probe extending within the passageway of the flexible body. The elongated probe has a distal end and includes an outer wall defining a channel. An access port, spaced proximally of the distal end, extends through the outer wall in communication with the channel. The method further includes moving the probe within the flexible body from a first position in which the access port is inside the passageway to a second position in which the access port is outside of the passageway.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

Figure 1:
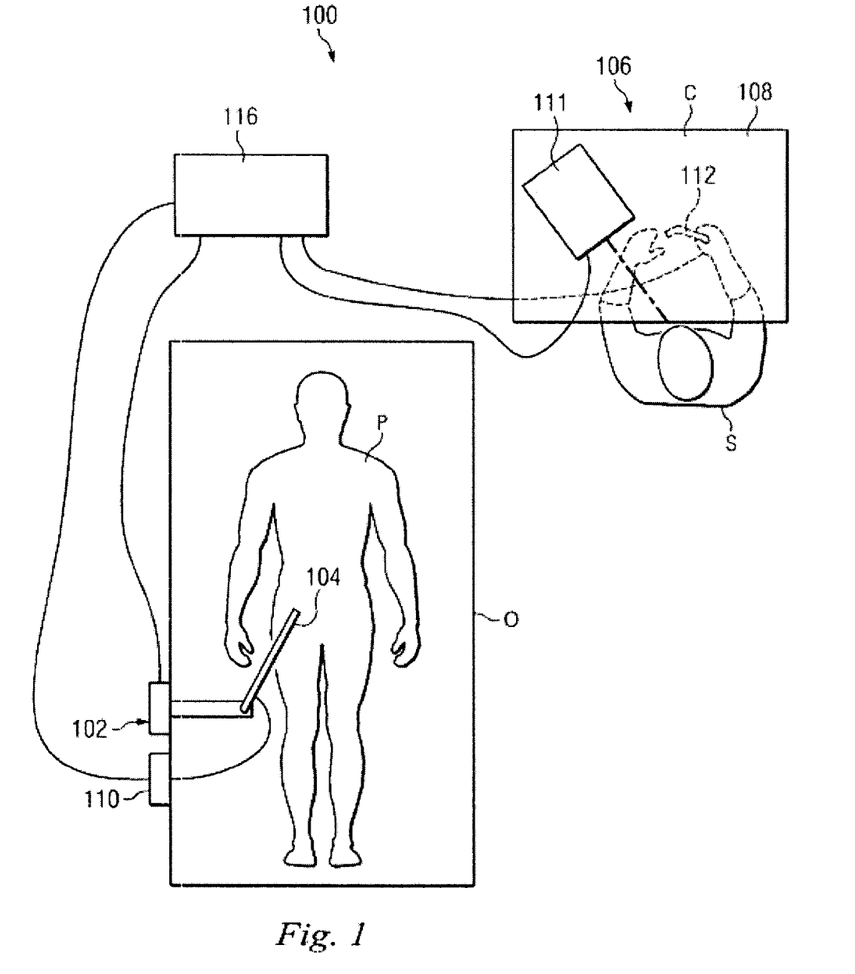
FIG. 1 is a diagrammatic top view of robotic surgical system, in accordance with embodiments of the present disclosure.

Referring to FIG. 1 of the drawings, a robotic surgical system is generally indicated by the reference numeral 100. As shown in FIG. 1, the robotic system 100 generally includes a surgical manipulator assembly 102 for operating a surgical instrument 104 in performing various procedures on the patient P. The assembly 102 is mounted to or near an operating table O. A master assembly 106 allows the clinician S (e.g., a surgeon or internist) to control the slave manipulator assembly 102.

The master assembly 106 may be located at a clinician's console C which is usually located in the same room as operating table O. However, it should be understood that the clinician S can be located in a different room or a completely different building from the patient P. Master assembly 106 generally includes an optional support 108 and one or more control device(s) 112 for controlling the manipulator assemblies 102. The control device(s) 112 may include any number of a variety of input devices, such as joysticks, trackballs, data gloves, trigger-guns, hand-operated controllers, voice recognition devices, body motion or presence sensors, or the like. In some embodiments, the control device(s) 112 will be provided with the same degrees of freedom as the associated surgical instruments 104 to provide the clinician with telepresence, or the perception that the control device(s) 112 are integral with the instruments 104 so that the clinician has a strong sense of directly controlling instruments 104. In other embodiments, the control device(s) 112 may have more or fewer degrees of freedom than the associated surgical instruments 104 and still provide the clinician with telepresence. In some embodiments, the control device(s) 112 are manual input devices which move with six degrees of freedom, and which may also include an actuatable handle for actuating instruments (for example, for closing grasping jaws, applying an electrical potential to an electrode, delivering a medicinal treatment, or the like).

In alternative embodiments, the robotic system may include more than one slave manipulator assembly and/or more than one master assembly. The exact number of manipulator assemblies will depend on the surgical procedure and the space constraints within the operating room, among other factors. The master assemblies may be collocated, or they may be positioned in separate locations. Multiple master assemblies allow more than one operator to control one or more slave manipulator assemblies in various combinations.

A visualization system 110 may include an endoscope system such that a concurrent (real-time) image of the surgical site is provided to clinician console C. The concurrent image may be, for example, a two- or three-dimensional image captured by an endoscopic probe positioned within the surgical site. In this embodiment, the visualization system 110 includes endoscopic components that may be integrally or removably coupled to the surgical instrument 104. In alternative embodiments, however, a separate endoscope attached to a separate manipulator assembly may be used to image the surgical site. Alternatively, a separate endoscope assembly may be directly operated by a user, without robotic control. The endoscope assembly may include active steering (e.g., via teleoperated steering wires) or passive steering (e.g., via guide wires or direct user guidance). The visualization system 110 may be implemented as hardware, firmware, software, or a combination thereof, which interacts with or is otherwise executed by one or more computer processors, which may include the processor(s) of a control system 116.

A display system 111 may display an image of the surgical site and surgical instruments captured by the visualization system 110. The display 111 and the master control device(s) 112 may be oriented such that the relative positions of the imaging device in the scope assembly and the surgical instruments are similar to the relative positions of the clinician's eyes and hand(s) so the operator can manipulate the surgical instrument 104 and the master control device(s) 112 as if viewing the workspace in substantially true presence. True presence means that the displayed tissue image appears to an operator as if the operator was physically present at the imager location and directly viewing the tissue from the imager's perspective.

Alternatively or additionally, display system 111 may present images of the surgical site recorded and/or modeled preoperatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. The presented preoperative images may include two-dimensional, three-dimensional, or four-dimensional (including e.g., time based or velocity based information) images.

In some embodiments, the display system 111 may display a virtual navigational image in which the actual location of the surgical instrument is registered (e.g., dynamically referenced) with preoperative or concurrent images to present the clinician S with a virtual image of the internal surgical site at the location of the tip of the surgical instrument.

In other embodiments, the display system 111 may display a virtual navigational image in which the actual location of the surgical instrument is registered with prior images (including preoperatively recorded images) or concurrent images to present the clinician S with a virtual image of a surgical instrument at the surgical site. An image of a portion of the surgical instrument may be superimposed on the virtual image to assist the clinician controlling the surgical instrument.

As shown in FIG. 1, a control system 116 includes at least one processor (not shown), and typically a plurality of processors, for effecting control between the slave surgical manipulator assembly 102, the master assembly 106, the visualization system 110, and the display system 111. The control system 116 also includes programmed instructions (e.g., a computer-readable medium storing the instructions) to implement some or all of the methods described herein. While control system 116 is shown as a single block in the simplified schematic of FIG. 1, the system may comprise a number of data processing circuits (e.g., on the slave surgical manipulator assembly 102 and/or on the master assembly 106), with at least a portion of the processing optionally being performed adjacent the slave surgical manipulator assembly, a portion being performed the master assembly, and the like. Any of a wide variety of centralized or distributed data processing architectures may be employed. Similarly, the programmed instructions may be implemented as a number of separate programs or subroutines, or they may be integrated into a number of other aspects of the robotic systems described herein. In one embodiment, control system 116 supports wireless communication protocols such as Bluetooth, IrDA, HomeRF, IEEE 802.11, DECT, and Wireless Telemetry.

In some embodiments, control system 116 may include one or more servo controllers to provide force and torque feedback from the surgical instruments 104 to one or more corresponding servomotors for the control device(s) 112. The servo controller(s) may also transmit signals instructing manipulator assembly 102 to move instruments which extend into an internal surgical site within the patient body via openings in the body. Any suitable conventional or specialized servo controller may be used. A servo controller may be separate from, or integrated with, manipulator assembly 102. In some embodiments, the servo controller and manipulator assembly are provided as part of a robotic arm cart positioned adjacent to the patient's body.

Each manipulator assembly 102 supports a surgical instrument 104 and may comprise a serial kinematic chain of one or more non-servo controlled links (e.g., one or more links that may be manually positioned and locked in place, generally referred to as a set-up structure) and a robotic manipulator. The robotic manipulator assembly 102 is driven by a series of actuators (e.g., motors). These motors actively move the robotic manipulators in response to commands from the control system 116. The motors are further coupled to the surgical instrument so as to advance the surgical instrument into a naturally or surgically created anatomical orifice and to move the distal end of the surgical instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors can be used to actuate an articulable end effector of the instrument for grasping tissue in the jaws of a biopsy device or the like.

Figure 2:
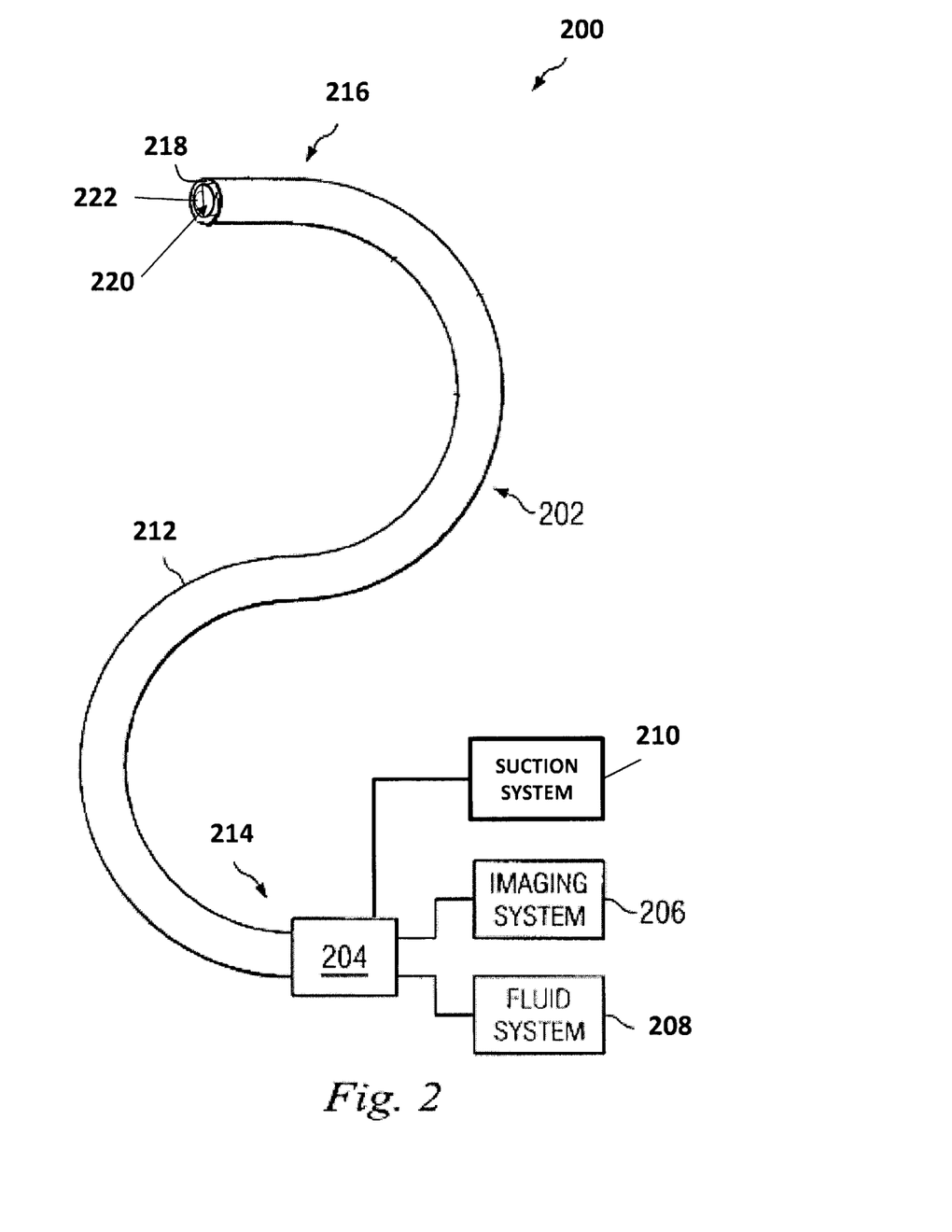
FIG. 2 illustrates an endoscopy system utilizing aspects of the present disclosure.

FIG. 2 illustrates an endoscopy system 200 utilizing aspects of the present disclosure. The endoscopy system 200 may be incorporated into a robotic surgical system, such as system 100 (e.g., as part of instrument 104), as part of the visualization and display system. Alternatively, the endoscopy system 200 may be used for non-robotic exploratory procedures or in procedures involving traditional manually operated surgical instruments, such as laparoscopic instruments. The system 200 includes an endoscopic probe 202 coupled by an interface unit 204 to one or more of an imaging system 206, a fluid system 208, a suction system 210, and other optional support systems (not shown), as deemed beneficial. The endoscopic probe 202 includes an elongated guide catheter 212 having a proximal end 214 and a distal end 216. The guide catheter 212 has an elongated flexible body. In one embodiment the guide catheter 212 has an approximately 2 mm outer diameter. Other guide catheter 212 outer diameters may be larger or smaller. The guide catheter 212 may be formed from a transparent, semi-transparent, or opaque material. The guide catheter 212 includes a passageway 218 that runs longitudinally through at least a portion of the length of the guide catheter. A vision probe 220 extends within the passageway 218. In various other embodiments, vision probe 220 may be provided and used without guide catheter 212.

The guide catheter 212 and/or vision probe 220 may be steerable or, alternatively, may be non-steerable with no integrated mechanism for operator control of the instrument bending. The guide catheter 212 and/or vision probe 220 may further house control mechanisms (not shown) for operating a surgical end effector or another working distal part that is manipulable for a medical function, e.g., for effecting a predetermined treatment of a target tissue. For instance, some end effectors have a single working member such as a scalpel, a blade, or an electrode. Other end effectors may include pair or plurality of working members such as forceps, graspers, scissors, or clip appliers, for example. Examples of electrically activated end effectors include electrosurgical electrodes, transducers, sensors, and the like.

FIG. 3-6 depict a cross-sectional view of the distal end of the guide catheter 212 and the vision probe 220. The vision probe 220 includes an outer wall 222 defining a working channel 224. At least a portion of the outer wall 222 defines a distal opening 225 at a distal face 220F of vision probe 220. An operational component such as an image capture instrument 226 extends within the channel 224. A fluid director 228 extends from the distal end of the outer wall 222. Details of the fluid director, structures for retaining the image capture instrument, and related structures and methods of use are provided in U.S. Pat. App. No. 61/658,305, filed Jun. 11, 2010, disclosing "Systems and Methods for Cleaning a Minimally Invasive Instrument," which is incorporated by reference herein in its entirety. Optionally, the fluid director may be eliminated such that no distal opening is present or the distal opening 225 is a straight opening.

The image capture instrument 226 includes a stereoscopic or monoscopic camera 230 for capturing images that are transmitted to and processed by the imaging system 206 for display. The image capture instrument 226 includes a cable 232 coupled to the camera 230 for transmitting the captured image data to the imaging system 206. Alternatively, the image capture instrument may be a coherent fiber-optic bundle, such as a fiberscope, that couples to the imaging system. The image capture instrument may be single or multi-spectral, for example capturing image data in the visible spectrum, or capturing image data in the visible and infrared or ultraviolet spectrums.

In one aspect, the remaining portion of the channel 224, not occupied by the instrument 226 or any other vision probes, can be a flow channel for material delivery or suction. Alternatively, the flow channel may be a discrete channel (e.g., a tubular member) extending through the vision probe 220.

One or more optional operational components 240 (FIG. 6) may extend within passageway 218 or the channel. Such additional components may include illumination components; steering controls such as cables or linkages to controllably bend the distal end of the vision probe and guide catheter; guide wires; stiffening members; preformed shapes; or tools such as needles and wipers or other cleaning accessories.

The channel 224 provides a transport pathway 233 from the fluid system 208 to, for example, convey an irrigation fluid to the surgical site, deliver a medication to the surgical site, provide insufflation, extract biopsied tissue or the like. The fluid system 208 may include pumps, fluid reservoirs, and other components for delivering fluids via the flow channel 228. The suction system 210 may include pumps, evacuation reservoirs, and other components for performing wet or dry suction through the flow channel 228. In aspects in which a discrete tubular member is not present to direct fluid flow, suctioned body matter, irrigation fluid (e.g., gas or liquid) or other flowable material (e.g., granular medication/therapeutic material, gel, mucus, or tissue) flows around and in contact with the image capture instrument 226 and/or the one or more other operational components. In this aspect, the image capture instrument 226 and any other operational components may be individually or collectively shielded, insulated, or otherwise protected from the surrounding fluid.

Use of the distal opening 225 as a suction port for clearing blockages from the image capture instrument 226 may be inadequate because the camera is larger than the cables 232 and thus obstructs a significant portion of the distal opening, restricting flow. Removing the image capture instrument 226 from the guide catheter 212 for cleaning or for suctioning through the guide catheter is also undesirable because vision is lost while the image capture instrument is removed.

In the embodiment of FIGS. 3-6, the distal end of vision probe 220 includes an access port 234 though the outer wall 222. The access port 234 is located proximally of the probe distal face 220F. Although access port 234 is shown partially aligned with camera 230 for exemplary purposes, in various embodiments, the port 234 may be located, for example, substantially aligned with camera 230, proximal or distal to camera 230, or spaced relative to a specific landmark, such as distal face 220F. At least a portion of the port 234 opens to an area of the channel 224 proximal of the camera 230. In this area of the channel 230, the image capture instrument 226 occupies less of the channel than it does at the distal end of the channel where the camera 230 is located. Thus, positioning the access port 234 proximally of the camera 230 allows for a much larger suction cross-sectional area than would an access port near the distal end of the probe. The access port 234 has a cross-sectional area that is generally larger than the unblocked cross-sectional area of the distal opening 225. In some embodiments, vision probe 220 can include a one-way flow controller such as an optional cover 236 that is hingedly or fixedly coupled to a portion of the outer wall 222. The cover 236 can be sized and shaped to extend over the access port 234 to block fluid migration therethrough when the cover is in a closed position. The cover may further include gaskets, seals, a perimeter lip, latches or other mechanisms to prevent migration of fluids through the access port when the cover is in a closed position.

In some embodiments, the cover 236 is a flap portion cut from the outer wall 222 and the hinge 238 is a bendable portion of the outer wall that continuously connects the outer wall to the cover. In other embodiments, the cover and hinge may be separately fabricated and coupled to the outer wall. For example, a duckbill valve may be used. The hinge can in some embodiments include a biasing member such as a spring, a shape memory material, or a preformed bend in the outer wall material that biases the cover towards a desired default position (e.g., covering or exposing port 234). For example, in various embodiments, the biasing member may bias the cover outward (away from channel 224) or inward (into the channel 224). The probe 220 may be a single use device or may be designed for resterilization and multiple uses.

Figure 3:
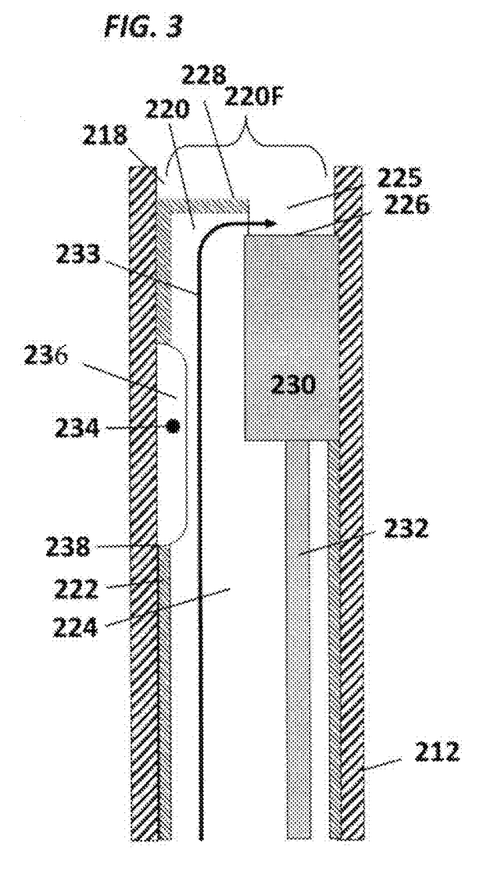
FIGS. 3-9 are cross-sectional views of various embodiments of a distal end of an endoscopy system.

FIG. 3 illustrates the distal end of the vision probe 220 withdrawn entirely into the passageway 218 of the guide catheter 212. If no cover 236 is present, the wall of catheter 212 can block and essentially close port 234. If cover 236 is present, it may be held in a closed position by the adjacent guide catheter 212—for example with the bias to move the cover 220 to the open position overcome by the wall of catheter 212.

In this "retracted" configuration, the fluid flow 233 from the fluid system 208 is primarily confined to and directed through the channel 224 until it reaches the fluid director 228. Typically, little or no fluid passes through the covered access port 234. The fluid flow 233 continues through the channel 224 until it impacts the fluid director 228. At a result of this impact, the fluid is directed toward and across the distal end of the camera 230 so that the fluid contacts and flows through the distal opening 225 of the probe, across the distal end of camera. The deflected fluid thus cleans the camera 230, ridding it of blood, mucous, tissue, or other material that may have accumulated and enabling the image capture instrument 226 to once again provide usable images. Alternatively, the fluid flow from the distal end 225 of the probe may be used to cool the camera 230 or deliver a fluid treatment to the adjacent body region.

Figure 4:
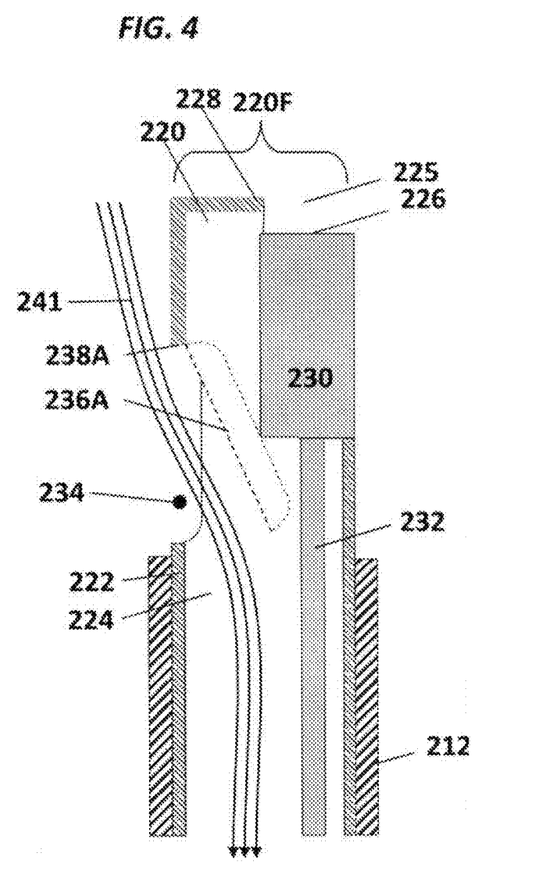

FIG. 4 illustrates the vision probe 220 extended from the passageway 218. The vision probe 220 may be advanced from the passageway 218 or the guide catheter 212 may be retracted away from the distal end of the vision probe. The access port 234 is now positioned at least partially distally of the guide catheter, thereby "opening" port 234. In this embodiment, the cover 236 is no longer held in a closed position by pressure from the guide catheter 212. This allows the biasing member of the hinge 238 to pivot the cover 236 away from the access port 234, allowing a through pathway from the channel 224 to the body region adjacent the distal end of the vision probe 220. When the suction system 210 is activated, a suction flow 241 is created to aspirate bodily matter including tissue, fluids, and gases from the adjacent body region through the access port 234 and channel 224.

In some embodiments, cover 236A may be present, and hingedly connected to the distal end of access port 234 as indicated in FIG. 4, such that the force of the suction overcomes a port closing bias at hinge 238A and cover 236A pivots into channel 224 about hinge 238A. This opens the access port 234 to create a flow channel for aspirating bodily matter including tissue, fluids, and gases from the adjacent body lumen. When the suction is removed, the biasing member returns cover 236A to a closed position blocking the access port 234. In alternative embodiments, a biasing member may be omitted.

Figure 5:
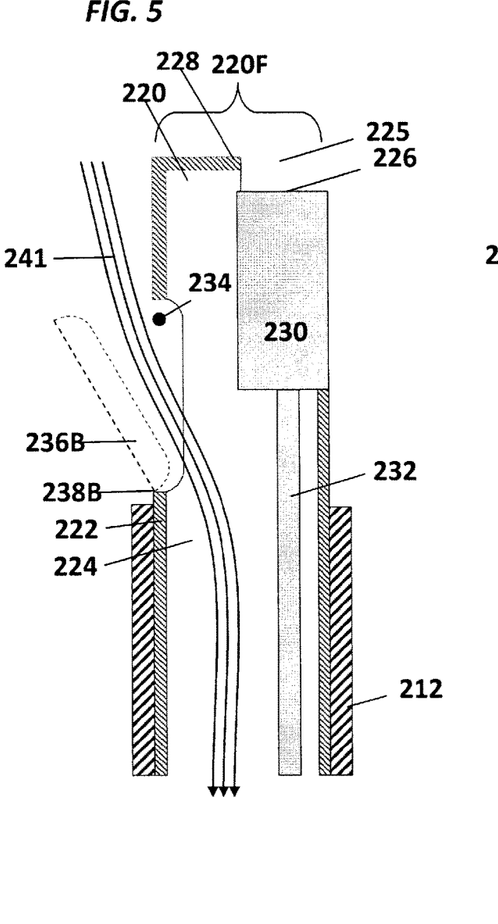

In various other embodiments, cover 236B may be present, and hingedly connected to the proximal end of access port 234 as indicated in FIG. 5. In such embodiments, the biasing member (e.g., a spring, a shape memory member, or preformed bend, as previously described) of the hinge 238 may be selected to bias cover 236B outward from probe 220 (i.e., opening port 234) and also to have a bias sufficient to prevent cover 236B from being drawn into a closed position or into the channel 224 by the created suction.

Figure 6:
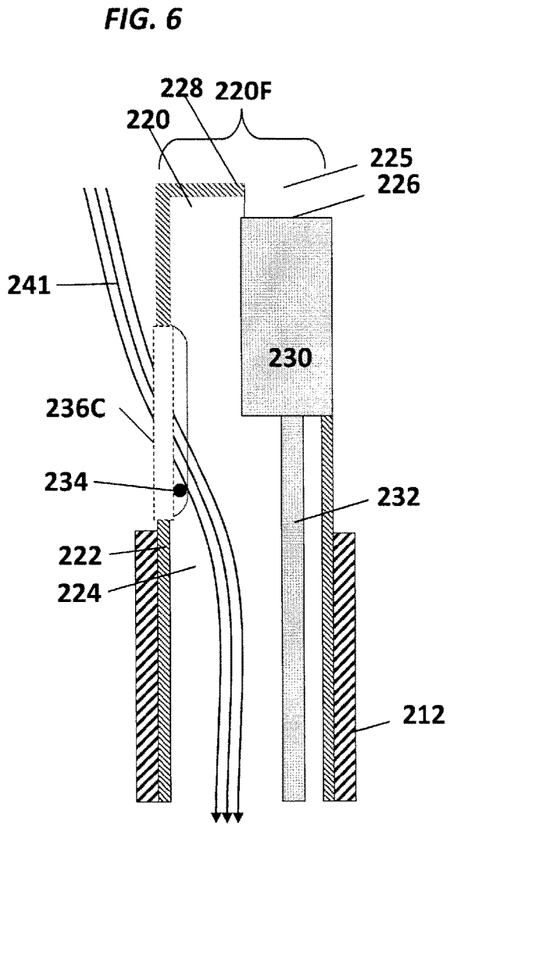

In various other embodiments, cover 236C may be present, and positioned in a stationary manner over port 234, such as indicated in FIG. 6. In such embodiments, stationary cover 236C is connected to the outer wall 222 blocking access to the channel 224 through the access port 234. The stationary cover 236C may include, for example, a check valve that prevents bodily matter from flowing into the channel 224 and prevents fluid flowing through the channel from exiting through the access port 234. When activated, for example, by the activation of the suction system, the valve opens to permit the flow of bodily material from the adjacent body region into the channel 224. Alternatively, the cover 236C may be a membrane that prevents bodily matter from flowing into the channel 224 and prevents fluid flowing through the channel from exiting through the access port 234. When suction is applied, the membrane permits the flow of bodily material from the adjacent body region into the channel 224.

With at least a portion of the access port 234 positioned proximally of the camera 230, the most of the suction flow 241 bypasses the flow restriction of at the distal end 225. Locating the access port proximally of the flow-obstructing camera 230 may be particularly useful for ultrathin probe implementations in which the probe is used to investigate or treat very narrow body lumens such as the bronchial passageways of the lung.

Figure 7:
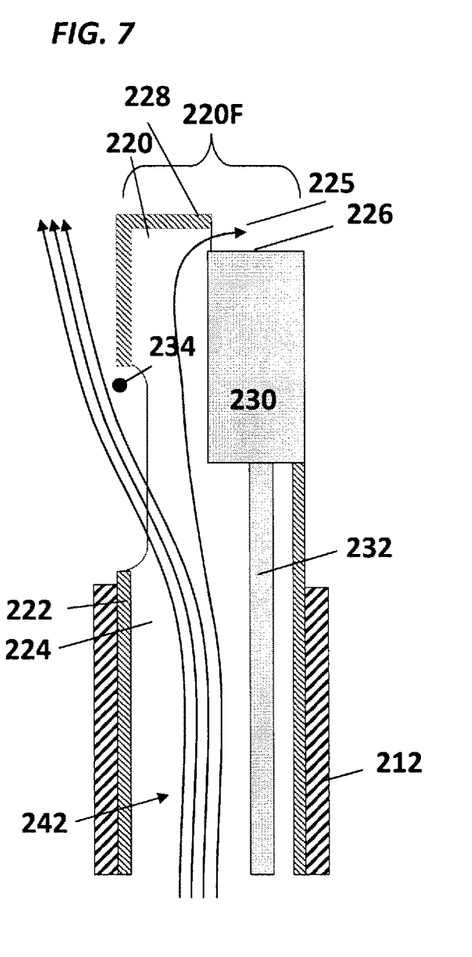

In some embodiments, fluid system 208 can activated to create a fluid flow path 242 that moves from channel 224 out at least partially through port 234, such as indicated in FIG. 7. This fluid flow moves through the access port 234 to, for example, irrigate the body region adjacent the component 220. Note that a portion of the fluid flow may also continue through the channel 224 and out through the distal opening 225 of the component 220. In various embodiments, the distal opening may be blocked causing the entire fluid flow to pass through the access port. In various embodiments, optional cover 236 may be present, such that the pressure from the fluid flow can cause cover 236 to open (e.g., proximally hinged cover 236B), or the bias at hinge 238 holds cover 236 open during such flow (e.g., distally hinged cover 23A).

Figure 8:
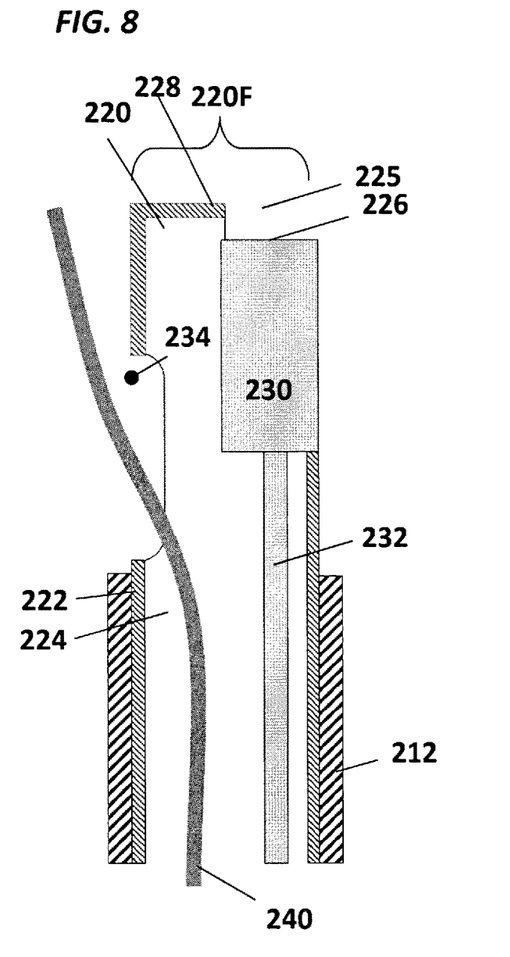

In some embodiments, an operational component 240 can be extended through the access port 234, such as indicated in FIG. 8. The operational component may be, for example, an illumination component; steering controls such as cables or linkages to controllably bend the distal end of the probe and/or guide catheter; guide wires; stiffening members; preformed shapes; or tools such as biopsy needles and wipers or other cleaning accessories. The presence of access port 234 can beneficially allow operational component 240 to have a larger cross-section than would be possible for a component deployed through the distal face of probe 220. In various embodiments, optional cover 236 may be present and in an open position due to the biasing member of the hinge 238 (e.g., distally hinged cover 236A). In other embodiments, optional cover 236 may be present such that as operational component 240 is advanced through the channel 224 and into contact with cover 236, the contact causes cover 236 to open (e.g., proximally hinged cover 236B). Optionally, the operational component 240 may be used in combination with the suction system 210 and/or the fluid system 208. For example, the operational component may be a cleaning tool extending through the access port 234. A saline fluid may be flushed through the channel 224 and out through the access port 234. Used together, the cleaning tool and the saline fluid may be used to remove stubborn debris deposits from the distal end of the guide catheter or vision probe.

Figure 9:
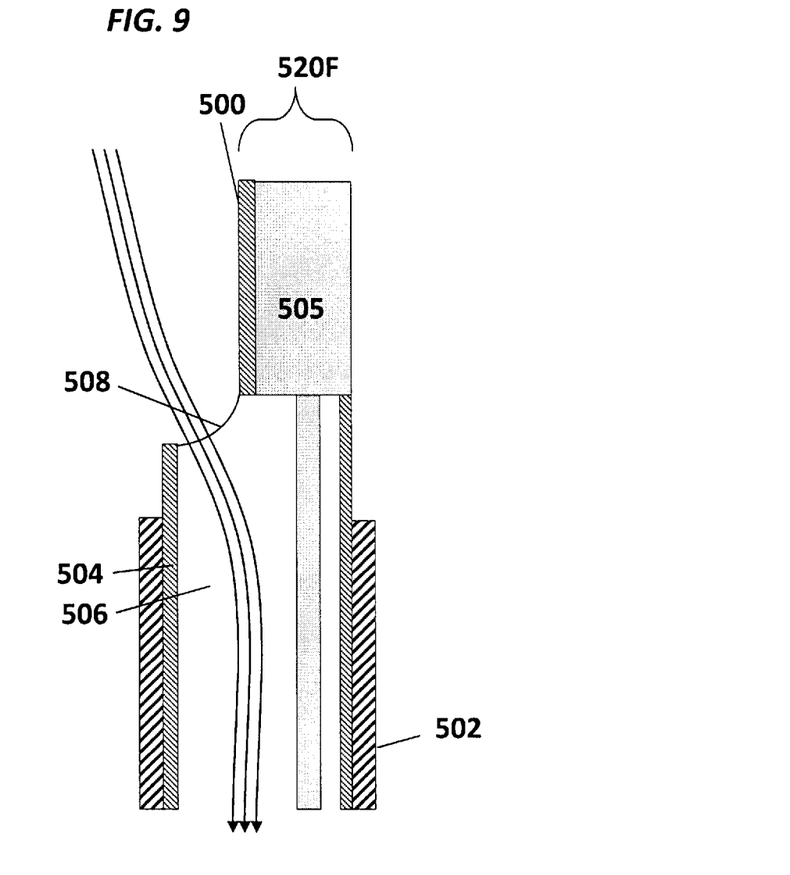

FIG. 9 illustrates a vision probe 500 extended from the interior passageway of a guide catheter 502. The vision probe 500 is substantially similar to the vision probe 220 except for the differences to be described. The vision probe 500 includes an outer wall 504 surrounding a channel 506. An access port 508 located at the distal end of vision probe 500, proximally of distal face 520F, provides a passage from the adjacent body region through the outer wall 504 to the channel 506. In this embodiment, the outer wall 504 abuts a camera 505, eliminating a distal end flow passage. In this embodiment, the outer diameter of the distal tip of the vision probe 500 is smaller than the outer diameter of the vision probe proximally of the access port 508. Thus the cross-sectional area of the access port may be larger to improve suction performance. In this embodiment, the access port 508 is uncovered. When the vision probe 500 is extended so that the access port 508 is positioned distally of the guide catheter 502 and the suction system is activated, bodily matter is aspirated from the adjacent body region, through the access port 508 and through the channel 502. As described previously for other embodiments, the access port 508 can also be used to dispense a fluid flow from the channel 502 into the adjacent body region or can be used to route operational components from the channel 502 and into the adjacent body region.

Figure 10:
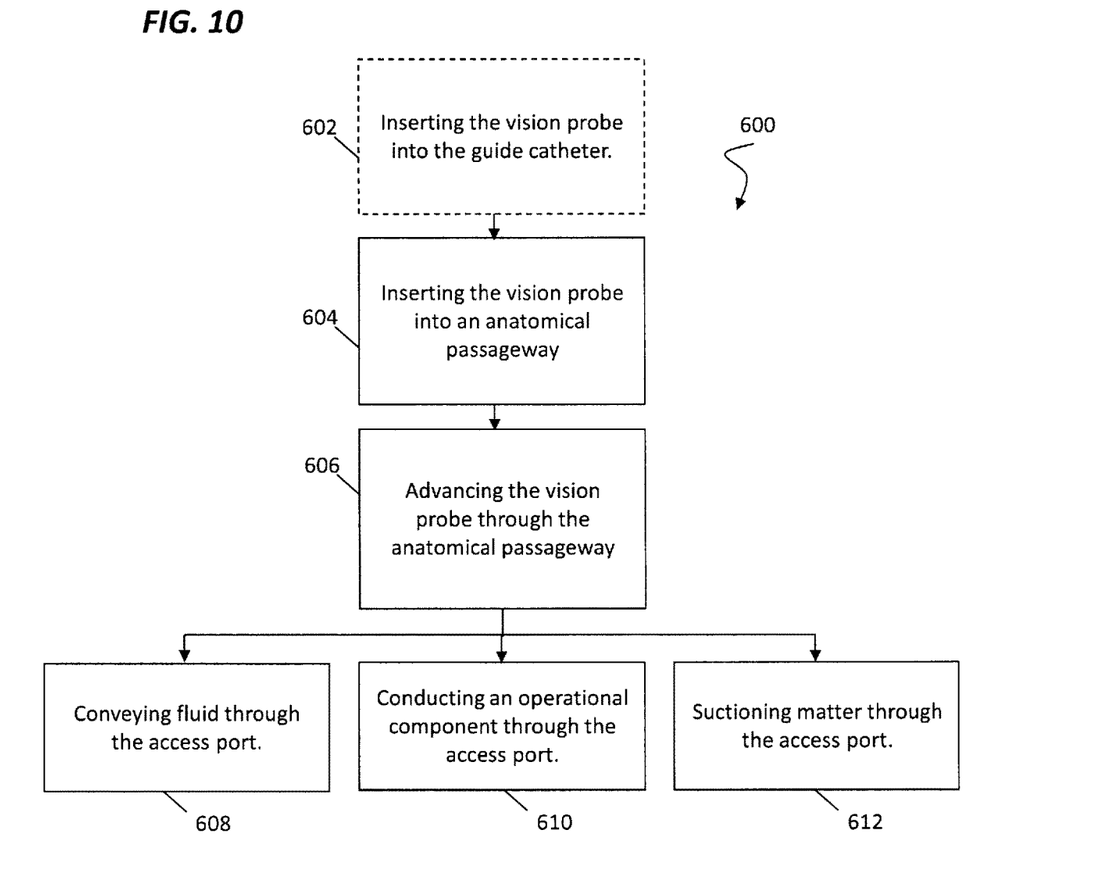
FIG. 10 is a flowchart illustrating a method of using an endoscopy system of this disclosure.

FIG. 10 provides a flowchart describing a method 600 of using the endoscopy system of the embodiments described above. At 602, the method includes optionally inserting the vision probe into the guide catheter, and at 604, the vision probe is inserted into an anatomical passageway. In some embodiments, the optional insertion of the vision probe into the guide catheter of 602 can be performed prior to the insertion of the combined vision probe/catheter into the anatomical passageway. In other embodiments, the optional insertion of the vision probe into the guide catheter of 602 can be performed after the insertion of the catheter into the anatomical passageway. In other embodiments, the optional insertion of the vision probe into the guide catheter of 602 can be performed after the vision probe has been at least partially inserted into the anatomical passageway (i.e., the guide catheter is advanced over the vision probe). In various other embodiments, 602 can be omitted and the vision probe can be inserted directly into the anatomical passageway.

At 606, the probe is advanced through the anatomical passageway. During this advancement, blood, tissue, mucous, or other matter may accumulate on the vision probe and obstruct its function. For example, matter accumulated on the vision probe may block all or part of the camera's field of view and make capturing a usable image impossible. Thereafter, one or more of the steps 608, 610, 612 may be taken to clean the vision probe or perform a clinical procedure within the anatomical passageway of the patient. Using any of the embodiments of FIGS. 3-9, the access port of the vision probe is opened to the anatomical passageway by opening a valve/cover and/or extending the distal tip of the vision probe outside of the guide catheter to expose the access port. Optionally, with the embodiment of FIG. 9, the procedures may be performed while the access port remains inside the guide catheter.

At 608, fluid (e.g., a saline solution, a gas, a therapeutic substance, a diagnostic or imaging material) is conveyed from the fluid system through the probe channel and out through the access port. Optionally, an access port cover may be opened to allow the fluid to exit the access port. If the vision probe has a distal opening in communication with the probe channel, a portion of the conveyed fluid may exit through the distal opening also. As the conveyed fluid flows distally through probe channel, it flows generally around and in contact with the image capture instrument. The conveyed fluid may be used to clean the exterior of the distal tip of the vision probe, dislodge blockages in the anatomical passageway, or irrigate/deliver a substance to the anatomical passageway.

At 610, an operational component (e.g., illumination components; steering controls; guide wires; stiffening members; preformed shapes; tools such as needles. forceps, brushes, and wipers or other cleaning accessories) are inserted through the probe channel and optionally out through the access port. Optionally, an access port cover may be opened to allow the operational component to exit the access port. The operational component extended through the access port may be used, for example, to clean the exterior of the distal tip of the vision probe, provide illumination for the camera, or deliver a treatment within the anatomical passageway.

At 612, a suction system is activated to pull bodily matter (e.g. blood, mucous, bone, tissue, gas), including matter that may be obstructing the vision probe, through the access port and into the probe channel, and optionally out through the proximal end of the channel. Optionally, an access port cover may be opened to allow the bodily matter to enter through the access port. With the location of the access port proximal of the camera of the image capture system, the amount of suction created through the channel is greater than would have been achieved using only the restricted distal tip opening of the vision probe.

Although the systems and methods have been described herein with respect to endoluminal probes, the systems and methods are also suitable for other applications in which in vivo cleaning of an instrument is advantageous. For example, the fluid delivery and cleaning systems and methods described may be suitable for use with ablation catheters, laser fibers, other minimally invasive instruments, or other types of endoscopic devices.

One or more elements in embodiments of the invention may be implemented in software to execute on a processor of a computer system such as control system 116. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. An anatomical probe system comprising:
   an elongated flexible body; and
   an elongated probe extending within the elongated flexible body and having a distal opening at a distal face of a distal end of the elongated probe, the elongated probe including:
      an outer wall defining a channel;
      an access port in the outer wall in communication with the channel, wherein the access port is spaced proximally of the distal face of the distal end;
      a one-way flow controller including a cover for the access port connected to the outer wall by a hinge, wherein the cover is configured to move between an open position where the access port is uncovered and the channel is in fluid communication with an area adjacent to the elongated probe via the access port to create fluid flow from the channel through the access port, and a closed position where the access port is covered and a migration of fluids through the access port is prevented while a migration of fluids through the distal opening is permitted; and
      an image capture instrument secured to the outer wall within the channel at a location proximal of the distal opening.

2. The anatomical probe system of claim 1 wherein the hinge includes a biasing member including a spring member to bias the cover towards a position within the channel or towards a position outside the channel.

3. The anatomical probe system of claim 1 wherein the cover is formed by cutting the outer wall to form the cover.

4. The anatomical probe system of claim 1 wherein the access port is positioned in the outer wall so as to partially overlap with the image capture instrument.

5. The anatomical probe system of claim 1 further comprising a suction source for aspirating at least one of bodily matter, tissue, fluids, or gases through the access port and the channel.

6. The anatomical probe system of claim 1 wherein a portion of the outer wall extends between the access port and the distal end.

7. The anatomical probe system of claim 1 further comprising a fluid director adapted to direct a fluid from the channel toward the image capture instrument when the cover is in the closed position.

8. The anatomical probe system of claim 1 further comprising a suction source for conveying at least one of bodily matter, tissue, gases or fluid through the channel and the access port towards a proximal end of the elongated probe.

9. The anatomical probe system of claim 1, further comprising a biasing member including a spring.

10. The anatomical probe system of claim 1, wherein when the elongated probe is retracted into the elongated flexible body the access port is covered, and wherein when the elongated probe is extended outward from the elongated flexible body the cover is capable of pivoting to the open position such that the access port is uncovered.

11. The anatomical probe system of claim 1, wherein the cover is configured to move from the closed position to the open position in response to a suction force in the channel.

12. An anatomical probe system comprising:
    an elongated flexible body having a passageway formed therein and a distal end that is freely movable and a proximal end coupled to an interface system;
    an elongated probe extending within the passageway of the elongated flexible body and having a distal opening at a distal face of a distal end of the elongated probe, the elongated probe including:
       an outer wall defining a central working channel,
       an image capture system having a camera affixed at a distal end of the image capture system,
       an access port in the outer wall in communication with the central working channel, wherein the access port is spaced proximally of the distal face, and
       a one-way flow controller including a cover for the access port connected to the outer wall by a hinge, wherein the cover is configured to move between an open position where the access port is uncovered and the central working channel is in fluid communication with an area adjacent to the elongated probe via the access port to create fluid flow from the central working channel through the access port, and a closed position where the access port is covered and a migration of fluids through the access port is prevented; and
    a suction source for conveying at least one of bodily matter, tissue, gases or fluid through the central working channel and the access port towards a proximal end of the elongated probe, wherein the cover is configured to move from the closed position to the open position in response to a suction force in the central working channel generated by the suction source.

13. The anatomical probe system of claim 12 wherein the camera is recessed from the distal end of the elongated probe.

14. The anatomical probe system of claim 13 wherein the image capture instrument is at least partially disposed within the central working channel.

15. The anatomical probe system of claim 13 further comprising a fluid director that directs fluid across a distal end of the camera, wherein an opening of the fluid director is disposed between the distal end of the elongated probe and the distal end of the camera of the image capture instrument.

16. The anatomical probe system of claim 12 wherein the cover is formed by a flap portion of the outer wall.

17. The anatomical probe system of claim 16 wherein the flap portion of the outer wall is coupled to the outer wall by the hinge, and wherein the hinge is formed from a bendable portion of the outer wall, the bendable portion continuously connecting the flap portion to the outer wall.

18. The anatomical probe system of claim 17 wherein the hinge includes a biasing member including a spring member to bias the cover towards a first position within the central working channel or towards a second position outside the central working channel.

19. The anatomical probe system of claim 12 wherein the elongated probe is retractable into a distal end of the elongate flexible body such that the distal face of the elongated probe is positioned within the passageway of the elongate flexible body.

* * * * *